(12) United States Patent
Barrett et al.

(10) Patent No.: US 8,333,724 B2
(45) Date of Patent: Dec. 18, 2012

(54) LOW FLOW OPTICAL BLOOD CHAMBER

(75) Inventors: Louis L. Barrett, West Point, UT (US); Perry N. Law, Centerville, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 150 days.

(21) Appl. No.: 12/876,798

(22) Filed: Sep. 7, 2010

(65) Prior Publication Data

US 2012/0059303 A1    Mar. 8, 2012

(51) Int. Cl.
*A61M 1/14* (2006.01)

(52) U.S. Cl. ........................................ 604/5.01

(58) Field of Classification Search .................. None
See application file for complete search history.

(56) References Cited

U.S. PATENT DOCUMENTS

| | | |
|---|---|---|
| 5,351,686 A | 10/1994 | Steuer et al. |
| 5,372,136 A | 12/1994 | Steuer et al. |
| 5,456,253 A | 10/1995 | Steuer et al. |
| 6,090,061 A | 7/2000 | Steuer et al. |
| 6,746,415 B1 | 6/2004 | Steuer et al. |
| 2005/0094127 A1 | 5/2005 | O'Mahony et al. |
| 2010/0110416 A1 | 5/2010 | Barrett et al. |

FOREIGN PATENT DOCUMENTS

| | | |
|---|---|---|
| WO | WO 93/06456 A1 | 4/1993 |
| WO | WO 01/93944 A1 | 12/2001 |

OTHER PUBLICATIONS

Blood Chamber 2001—Admitted Prior Art.
CL Photo 2000—Admitted Prior Art.
Blood Chamber Instruction Sheet 2001—Admitted Prior Art.

*Primary Examiner* — Melanie Hand
*Assistant Examiner* — Andrew S Lo
(74) *Attorney, Agent, or Firm* — Leydig, Voit & Mayer, Ltd.

(57) ABSTRACT

A low flow blood chamber for optically monitoring blood flowing through extracorporeal tubing has a flat elongated blood flow cavity but preserves the circular viewing area of conventional blood chambers. The blood chamber provides consistent, mixed flow through the blood cavity even at low blood flow rates, e.g. 10 to 500 ml/min., while maintaining certain dimensional characteristics of conventional blood chambers.

12 Claims, 5 Drawing Sheets

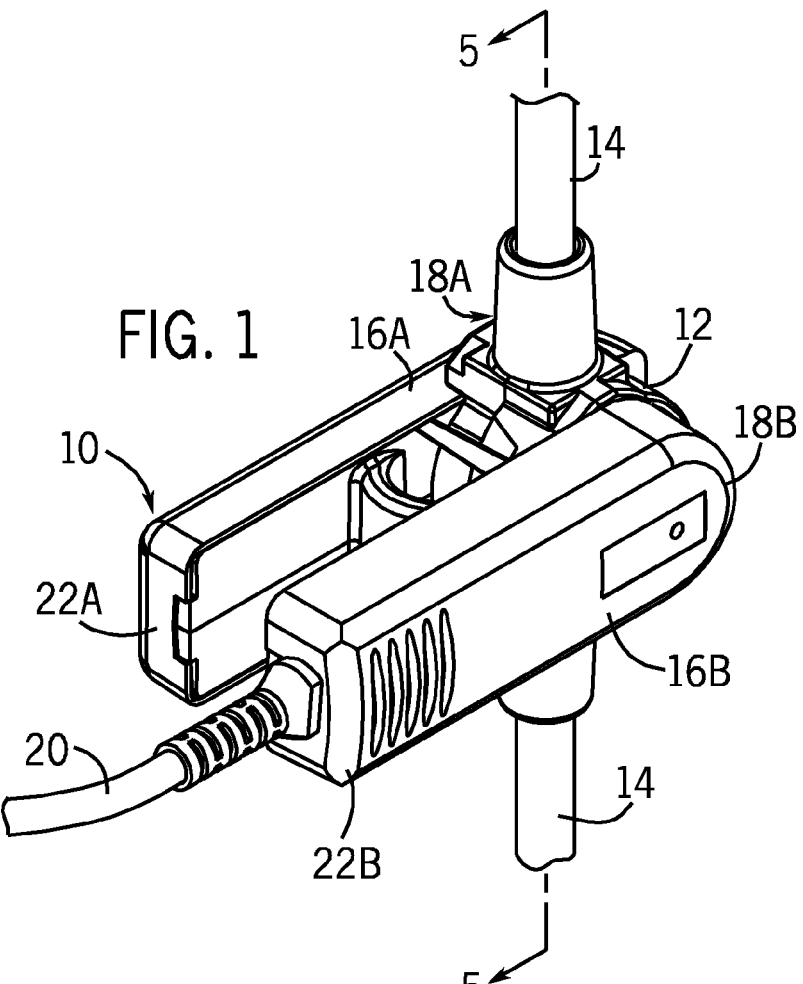
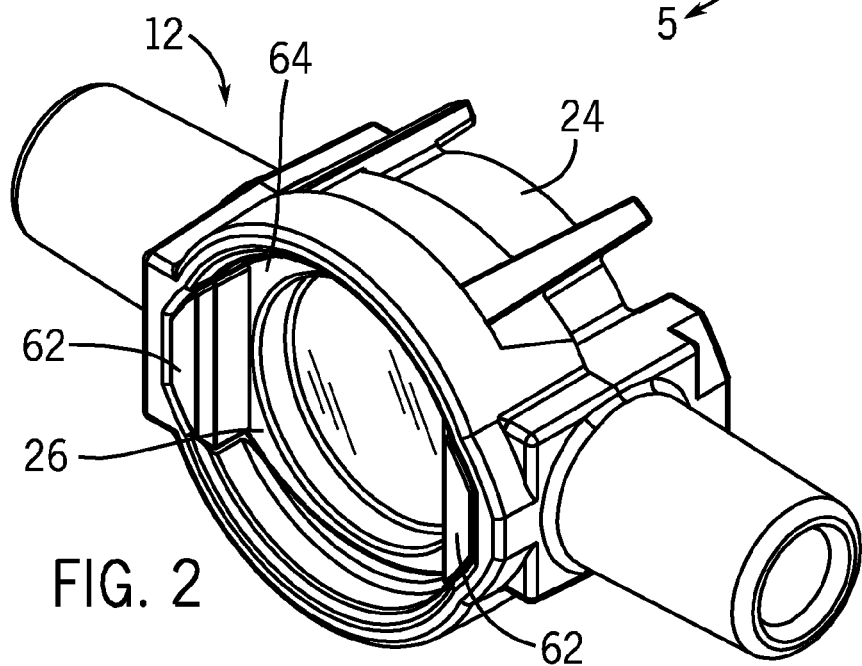

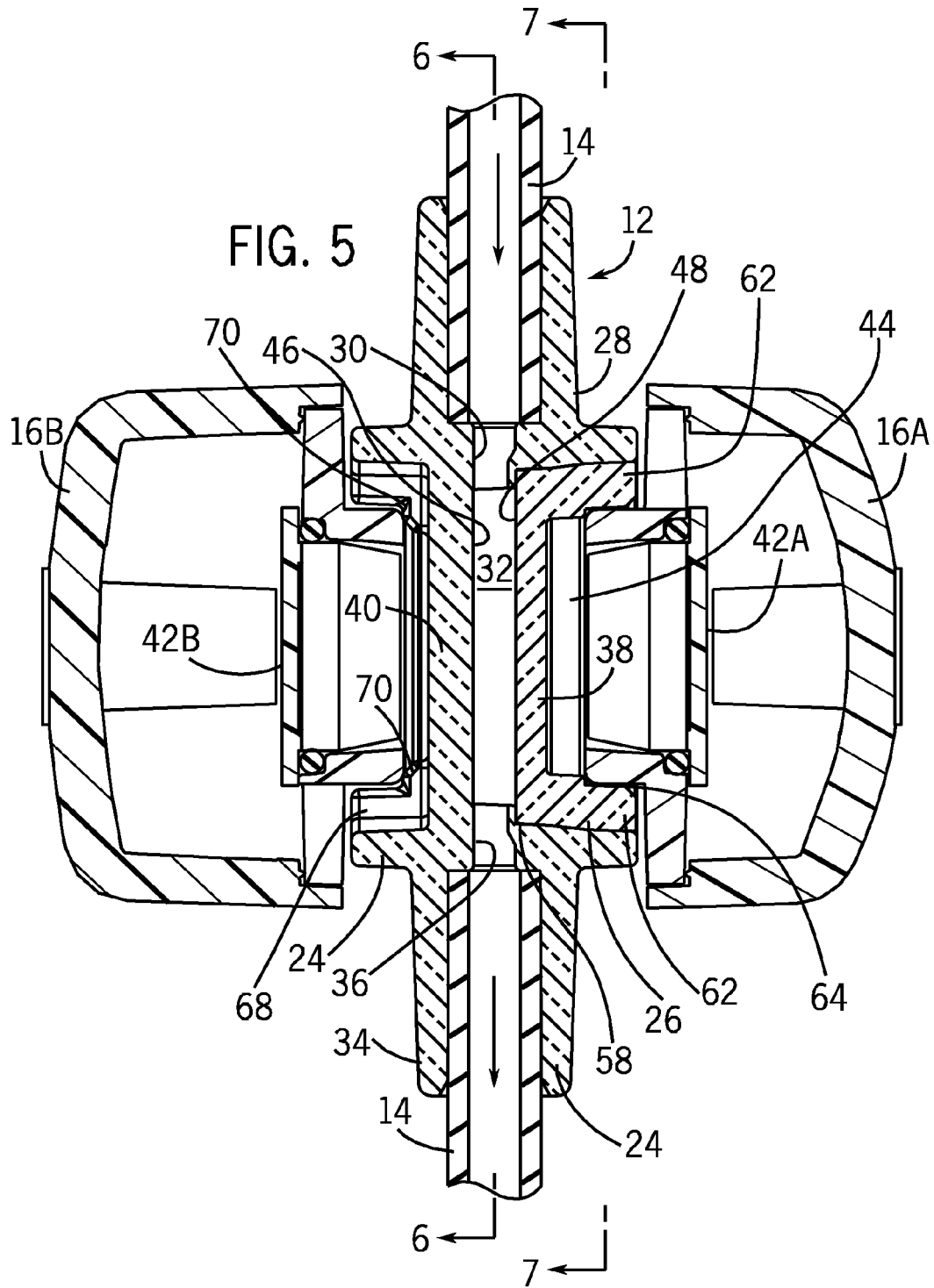

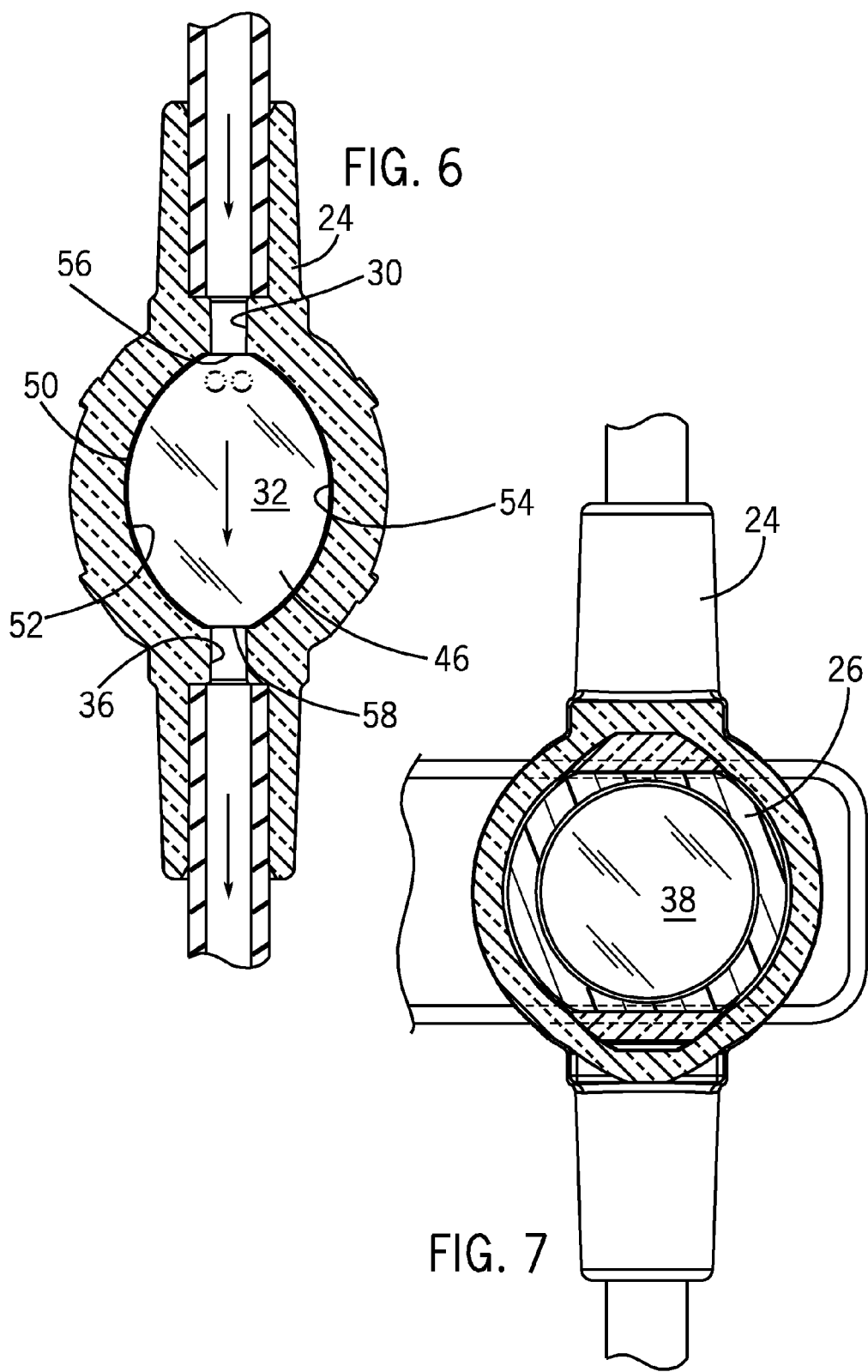

US 8,333,724 B2

LOW FLOW OPTICAL BLOOD CHAMBER

FIELD OF THE INVENTION

The invention relates to an extracorporeal blood chamber in an optical blood monitoring system. The invention is particularly useful in low blood flow applications, for example 10 to 500 ml/min.

BACKGROUND OF THE INVENTION

Optical blood monitors have been widely used in connection with conventional intermittent hemodialysis systems in which extracorporeal blood flow rate is typically in the range of 200 to 1500 ml/min. Optical blood monitors measure the patient's hematocrit value and/or oxygen saturation level in real time. It is well known that the change in blood volume is inversely proportional to the hematocrit value and also that the hemoglobin level can be estimated from the hematocrit value.

Applicants' assignee sells the Crit-Line® optical blood monitoring system. The Crit-Line® blood monitoring system uses optical techniques to non-invasively measure in real time the hematocrit level (HCT) of blood flowing through extracorporeal tubing, normally ¼" tubing associated with a dialysis machine. In the Crit-Line® system, a sterile, single-use blood chamber is attached inline to the extracorporeal tubing usually located on the arterial side of the dialyzer. The blood chamber provides a viewing point for optical sensors. Multiple wavelengths of visible and infrared light are directed through the blood chamber and the patient's blood flowing through the blood chamber, and a photodetector measures the resulting intensity of light at each wavelength. The preferred wavelengths are about 810 nm (e.g. 829 nm), which is substantially isobestic for red blood cells, and about 1300 nm, which is substantially isobestic for water.

A ratiometric technique is implemented in the Crit-Line® controller to calculate the patient's hematocrit value in real time. The ratiometric technique is substantially disclosed in U.S. Pat. No. 5,372,136 entitled "System and Method for Non-invasive Hematocrit Monitoring", which issued on Dec. 13, 1999 and is also assigned to the assignee of the present application. The hematocrit value (HCT) is defined as the percentage determined by dividing the volume of red blood cells in a given whole blood sample by the overall volume of the blood sample. A screen on the Crit-Line® controller typically displays a graph showing the percentage change in blood volume during a dialysis treatment session. The Crit-Line® system can also measure, optically, the oxygen saturation level in the blood flowing through the dialysis system as related to the patient's condition.

Typically, the photoemitters and detector are located in a clip assembly that clips over the viewing area for the blood chamber. An electrical cable connects the head of the clip to the controller, which is located near the patient and near the hemodialysis machine. The clip assemblies are calibrated at the factory, and it may be necessary to recalibrate the clip assemblies from time to time, as described in co-pending patent application Ser. No. 12/265,392, filed Nov. 5, 2008, entitled "Measuring Hematocrit and Estimating Hemoglobin Values with a Non-Invasive, Optical Blood Monitoring System", incorporated by reference herein. The calibration of the clip assembly depends at least in part on the configuration of the blood chamber viewing area.

The Crit-Line® blood chamber that is in use today includes an inlet port and channel which lead to an internal blood flow cavity and an outlet channel and port which lead away from the cavity for the blood to exit the blood chamber. Connectors commonly called luer locks are provided to connect the blood chamber to extracorporeal tubing or a dialysis filter as required. The internal blood flow cavity is defined by two circular flat walls that are parallel to one another and set apart at a predetermined fixed distance. It is important that the thickness of the lenses in the viewing area as well as the predetermined fixed distance between the lenses be tightly controlled during manufacturing inasmuch as calibration of the sensing assembly and controller depends on these dimensions. The blood chamber comprises a molded, clear polycarbonate chamber body which includes an integral viewing lens on one side of the blood flow cavity. A lens body including the clear polycarbonate lens is sonically welded to the chamber body and provides a viewing lens on the other side of the blood flow cavity. A moat providing a ring of thicker blood depth surrounds the circular internal blood flow cavity. One of the primary purposes of the moat is to protect visible and infrared light from ducting through the body of the blood chamber directly to the photodetector(s); rather than passing through a direct path from the photoemitter to the detector through the blood flow. The blood chamber also includes two turbulence posts located in the vicinity of the location where the inlet channel opens into the circular blood flow cavity. The purpose of the turbulence post is to establish standing eddy currents within the circular blood flow cavity in order to provide a reliable, homogeneous blood flow through the viewing area. When designing the blood flow path through the blood chamber, it is important to eliminate or minimize the propensity for blood to clot in the blood chamber, and also eliminate the possibility of hemolysis as the blood flows into and through the blood chamber. The current Crit-Line® blood chamber, as described, is designed to accommodate flow rates of about 100 ml/min. to 1500 ml/min. through ¼" extracorporeal tubing. Under these conditions, the current design has been found to provide safe, consistent, homogeneous flow through the blood chamber (without clotting and hemolysis problems) which in turn leads to accurate hematocrit and blood volume data.

As mentioned, the photoemitters and detector(s) are contained in a clip assembly that clips over the blood chamber on either side of the chamber walls forming the internal blood cavity and viewing lenses. The outer surfaces of the blood chamber include detents that provide access for the faces of the sensor assembly to rest against the outer flat surface of the respective viewing lens or be spaced a fixed distance from the viewing lens as the case may be. The shape of the detents is configured such that the clip assembly can fit onto the blood chamber only in a pre-selected geometric orientation in which the photoemitters and detector(s) are aligned in known positions.

It is an object of the invention to provide an optical blood chamber suitable for use in low flow applications, e.g. 10 ml/min. to 500 ml/min. flowing through ⅛" extracorporeal tubing, such as low flow kidney dialysis or aquaphoresis treatments such as for preventing congestive heart failure. It is a further object of the invention to develop such a low flow blood chamber that is compatible for use with the existing sensor clip assemblies and control systems.

SUMMARY OF THE INVENTION

The invention is a low flow blood chamber for optically monitoring blood flowing through extracorporeal tubing. In its preferred form, the chamber includes a flat, generally elongated internal blood flow cavity, but preserves the circular viewing area of the prior art blood chambers. A blood chamber configured in accordance with the disclosed invention provides consistent, non-laminar flow through the cavity even at low blood flow rates, e.g. 10 to 500 ml/min., while maintaining certain dimensional characteristics of the prior art blood chambers. For example, the distance across the blood flow cavity between the viewing lenses remains the same (e.g. 0.080 to 0.086 inches), as does the thickness of the lenses of the blood chamber (e.g. 0.055 to 0.065 inches and 0.085 to 0.095 inches) and the distance between the photoemitters and detector(s) when the optical clip sensor assemblies are mounted on the blood chamber (e.g. 0.245 to 0.255 inches). The concurrence of these dimensions enables a blood chamber constructed in accordance with the invention to be used with the controller and sensor clip assemblies that can be calibrated for use with prior art blood chambers.

More specifically, the blood chamber comprises a chamber body preferably made of molded polycarbonate, and a lens body again preferably made of molded polycarbonate. The lens body is attached to the chamber body, via sonic welding or otherwise, to form the internal blood flow cavity. The chamber body includes a first port and channel in fluid communication with the internal blood flow cavity and a second port and channel axially aligned with the first port and channel and on the opposite side of the blood flow cavity. The chamber body includes a flat internal wall with a first perimeter edge and a second perimeter edge. The perimeter edges are preferably arcuate so that the flat internal wall resembles the shape of an oval. The chamber body also includes an internal peripheral wall that extends generally perpendicularly from and around the edge of the flat internal wall. The peripheral wall preferably includes first and second arcuate portions commensurate with the first and second arcuate perimeter edges on the flat internal wall in the chamber body. The peripheral wall includes a first opening to provide fluid communication between the first port and channel and the internal blood flow cavity. The peripheral wall also includes a second opening which provides fluid communication between the second port and channel and the internal blood flow cavity. As mentioned, the second port and channel are in axial alignment with the first poll and channel across the internal blood flow cavity. In accordance with the invention, the axial distance across the blood chamber between the first and second openings in the peripheral wall is greater than the maximum perpendicular distance across the blood flow cavity between the first and second portions of the peripheral wall. However, the distance between the peripheral walls must be sufficient to provide a full viewing area for the sensor assembly as discussed more below.

The lens body is configured with a flat internal wall such that, when the lens body is attached to the chamber body, the flat internal wall on the lens body forms the internal blood flow cavity with the flat internal wall and the peripheral wall on the chamber body. The lens body is attached to the chamber body with the flat internal wall on the lens being substantially parallel to the flat internal wall on the chamber body and also being separated from the flat internal wall in the chamber base by a predetermined fixed distance. As mentioned, it is preferred that this predetermined fixed distance be the same fixed distance that is used in conventional blood chambers designed for blood flows of 100 to 1500 ml/min.

Both the lens body and the chamber body include clear lenses. The lenses preferably have the same (or compatible) dimensions in terms of diameter (e.g. 0.475 to 0.485 inches) and thickness as conventional blood chambers. Although the conventional sensor assembly may not require the entire area of the lenses for robust viewing, it is desirable that the distance between the peripheral walls of the internal blood flow chamber be sufficient to provide a full field of view for a conventionally sized circular lens. Both the lens body and the chamber body have an outside surface with a detented receiving ledge that is designed to accept one side of a standard optical clip assembly. The preferred lens body has a shape resembling an oval and includes first and second upstanding pedestals extending outward from the detented receiving ledge. The pedestals are located peripheral of the circular viewing lens towards the respective port on the chamber body. The pedestals facilitate guidance of the clip assembly into proper alignment on the blood chamber. For a similar purpose, the chamber body includes multiple upstanding fingers spaced around the periphery of the detented receiving ledge on the chamber body. The chamber body also includes other guide walls for the purpose of guiding the clip assembly into proper alignment.

It has been found that a generally oval-shaped flow chamber provides a consistent non-laminar homogeneous flow through the viewing area without the need for turbulence posts to create standing eddy currents, even at low rates (e.g. 10 to 500 ml/min.). The ability to remove the post simplifies manufacturing. It also enables the blood chamber to be symmetric with respect to the direction of flow, which in turn simplifies installation of the blood chamber in the field.

Note that the present invention does not require a moat around the internal blood flow cavity, although a moat may be included if desired. In one embodiment of the invention, the chamber body includes a clear polycarbonate lens but the remainder of the chamber body is made of an opaque polycarbonate material in order to eliminate light ducting from the photoemitters through the chamber body directly to the photodetector(s). The entire lens body is preferably made of clear polycarbonate in this embodiment, although it would be possible for the lens body to have a clear polycarbonate lens viewing area with the remainder of the lens body being made of an opaque polycarbonate.

As mentioned, a blood chamber constructed in accordance with the preferred embodiment of the invention is designed to connect to ⅛" extracorporeal tubing, rather than conventional ¼" tubing. It is contemplated, however, that various aspects of the invention may be employed in blood chambers designed to connect to extracorporeal tubing larger than ⅛" tubing, as well as in applications in which extracorporeal blood flow rate is greater than the described 10 to 500 ml/min. A further alternate embodiment may replace one or both tubing interfaces with industry standard luer lock connectors for convenience in mechanically connecting to the blood chamber.

BRIEF DESCRIPTION OF THE DRAWINGS

FIG. 1 shows a low flow optical blood chamber constructed in accordance with the preferred embodiment of the invention being installed in extracorporeal tubing, and a conventional optical sensor clip assembly clipped onto the blood chamber.

FIG. 2 is a perspective view of a first side of the low flow optical blood chamber shown in FIG. 1.

FIG. 5 is a longitudinal sectional view taken along line 5-5 in FIG. 1.

FIG. 6 is a sectional view taken along line 6-6 in FIG. 5.

FIG. 7 is a sectional view taken along line 7-7 in FIG. 5.

DETAILED DESCRIPTION

FIG. 1 illustrates a conventional optical sensor clip assembly 10 installed on a low flow optical blood flow chamber 12 constructed in accordance with the invention. Tubing 14 is attached to the blood chamber 12. In accordance with the preferred embodiment of the invention, the tubing is ⅛" clear, medical grade polypropylene tubing appropriate for use in the peristaltic pump.

The sensor clip assembly 10 includes two arms 16A, 16B forming a spring-biased, jaw-like structure. The handles 22A, 22B on the sensor assembly arms 16A, 16B can be squeezed together against the spring bias to spread the heads 18A, 18B of the sensor assembly to install or remove the sensor assembly on the blood chamber 12. Photoemitters located in the head 18A of arm 16A emit visible and infrared light, e.g. at about 810 nm, 1300 nm and 660 nm. One or more photodetectors are located in the head 18B of arm 16B. An electrical cable 20 connects the sensor assembly to a system controller (not shown). As mentioned, the system controller calculates the patient's hematocrit value, and preferably oxygen saturation value, in real time using ratiometric techniques substantially disclosed in U.S. Pat. No. 5,372,136 entitled "System and Method for Non-invasive Hematocrit Monitoring", issuing on Dec. 13, 1999 and assigned to the assignee of the present invention, herein incorporated by reference. More specifically, the measured infrared intensity of the photodetector at about 1300 nm and 810 nm are used to determine the hematocrit value, whereas the intensities at about 810 nm and 660 nm are used to determine oxygen saturation levels. In both cases, the determined values for hematocrit and oxygen saturation value are determined in the controller by a mathematical ratiometric function. However, each pair of controller and sensor clip assembly 10 must be calibrated before use. Controller and sensor clip assemblies 10 are normally calibrated for use at the manufacturing facility with conventional blood chambers having standardized dimensions as discussed previously. Controller and sensor clip assemblies for low flow applications can be calibrated in similar fashion. It is possible to also apply a mathematical correction to the conventional blood chamber calibration to match the calibration for this low flow blood chamber.

Figure 3:
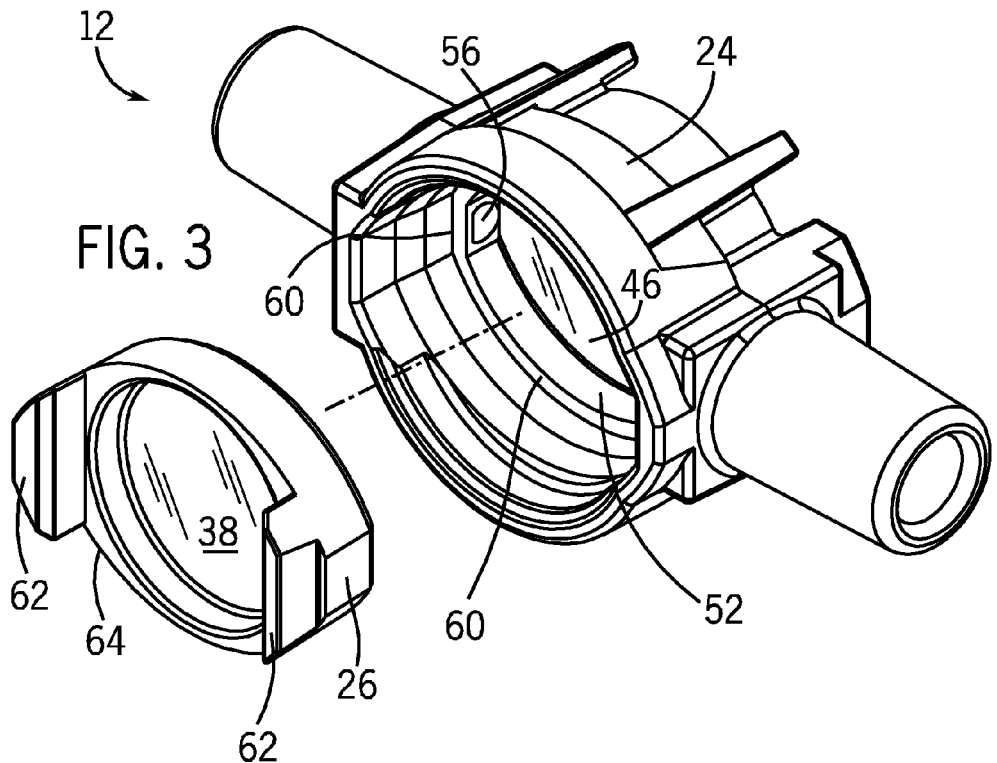
FIG. 3 is an assembly view similar to FIG. 2 showing the lens body exploded away from the chamber body.
Figure 4:
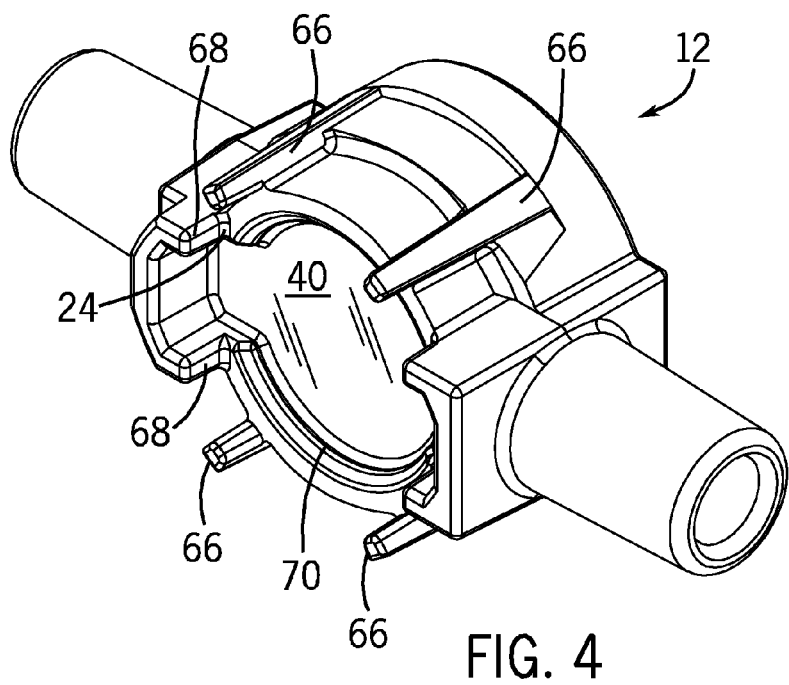
FIG. 4 is a perspective view of the low flow optical blood chamber taken from the other side of the blood chamber.

Referring to briefly to FIGS. 2-4, the blood chamber 12 shown is molded from medical grade clear polycarbonate, e.g. Bayer Makrolon FCR2458-55115 (no regrind allow), which is blood contact approved, USP XX11, Class V1. It is expected that the material be certified as to grade number, lot number and date of manufacture. No mold release should be used, and any lubrications should be food grade and not silicon based. The molded parts should be produced with no loose foreign material greater than 0.1 mm² and no embedded foreign material greater than 0.2 mm². The mold finish is preferably SPIA3 (scale) except along the surfaces for the viewing windows in which the finish is preferably at least SPIA1. Moreover, the viewing windows should contain no splay, bubbles or marks when looking through the display window viewed from 12" with the normal eye. Parts should be cleaned and free of dirt, oils and other foreign matters before use. The blood chamber 12 includes two molded parts, namely a chamber body 24 and a lens body 26. A lens body 26 is preferably sonically welded to the chamber body 24, although the lens body 26 may be secured to the chamber body 24 with medical grade adhesive if desired. In any event, it is especially important that the lens body 26 be attached to the chamber body 24 to provide leak-free blood flow chamber 12. For this reason, it is important there to be sufficient dimensional interference between the lens body 26 and the chamber body 24.

Referring to FIG. 5, the chamber body 24 has a first port 28 and channel 30 that are in fluid communication with the blood flow cavity 32. The chamber body 24 also has another port 34 and channel 36 in fluid communication with the blood flow cavity 32. Tubing 14 is secured to the inside wall of the ports 28, 34 using medical grade adhesive. The inside diameter across the channels 30, 36 is essentially equal to the inside diameter of the ⅛" tubing 14. The blood chamber 12 shown in FIG. 5 is symmetric with respect to the direction of blood flow. Assuming that the blood flow is in the direction depicted by the arrows in FIG. 5, the blood flow path comprises blood flowing through the tube 14 adhered to port 28 into the channel 30, consequently into and through internal blood cavity 32, and then through channel 36 and tubing 14 located in port 34.

The blood flow cavity 32 provides a viewing area for optically monitoring the blood as it passes between the circular viewing lens 38 in lens body 26 and circular viewing lens 40 in the chamber body 24. Photoemitters 42A are mounted within arm 16A of the sensor clip assembly 10. One or more photodetectors 42B are mounted to the arm 16B of the sensor clip assembly 10. Visible or infrared light emitted from the photoemitter 42A propagates space 44 and through the circular viewing lens 38 on the lens body 26 through blood flowing through the blood flow cavity 32, through the circular viewing lens 40 on the chamber body 24, and then the light intensity is detected by photodetector 42B. The blood flow cavity 32 is defined in part by a flat internal wall 46 on the chamber body 24 and another flat internal wall 48 on the lens body 26. The flat internal walls 46, 48 parallel to one another, and spaced apart from one another at a predetermined standardized distance (e.g. 0.080 to 0.086 inches), preferably selected to be commensurate with conventional blood flow chambers designed for flow rates of 100 ml/min. to 1500 ml/min. that are typically used with ¼" tubing. Also, it is preferred that the thickness of the respective viewing lenses 38, 40 and the distance across the space 44 be chosen to be consistent with conventional blood flow chambers. For example, the preferred thickness of lens 40 is between 0.085 and 0.095 inches, the preferred thickness of lens 38 is between 0.055 and 0.065 inches, and the preferred distance between the face of the photoemitter 42A and the face of the photodetector 42B is about 0.76 inches. While the specific dimensions in this regard are not important, the congruence of these dimensions with conventional blood flow chambers designed for higher blood flow rates enables low flow blood chambers 12 constructed in accordance with the invention to be used with a controller and sensor clip assembly 10 that has been calibrated for use with a conventional blood chamber with little or no modification of the calibration other than a simple mathematical adjustment, if required.

Referring now to FIG. 6, in accordance with the invention, the blood flow cavity 32 has an elongated shape, preferably resembling the shape of an oval. As mentioned, the chamber body 24 includes a flat internal wall 46. The flat internal wall 46 preferably has a substantially oval shape as shown in FIG. 6. In the preferred embodiment, the flat internal wall includes a first arcuate shaped perimeter edge 52 and a second arcuate shape perimeter edge 54. The chamber body 24 also includes a peripheral wall 50 that extends generally perpendicular from and around the perimeter edge of the flat internal wall 46. The peripheral wall 50 includes portions commensurate with the first and second perimeter arcuate shaped edges 52, 54 of the flat internal wall 46. The peripheral wall 50 also includes a first opening 56 that provides a fluid passageway between the channel 30 and the blood flow cavity 32, as well as a second opening 58 that provides a fluid passageway between the blood flow cavity 32 and the channel 36. The openings 56 and 58, as well as the channels 30, 36, are in axial alignment along an axis across the blood flow cavity 32. The distance across the blood flow cavity 32 between the first and second openings 56, 58 in the peripheral wall 50 is greater than the maximum distance perpendicular to the axis across the blood flow cavity 32 between the arcuate portions of the peripheral wall 50 corresponding to the first arcuate perimeter edge 52 and the second arcuate perimeter edge 54 of the flat internal wall. 46. As shown in FIG. 6, and as described herein, it is preferred that the first and second portions of the peripheral wall of the chamber body be arcuate; however, it is believed that aspects of the invention may be implemented without requiring that the first and second portions of the peripheral wall of the chamber body be arcuate. To carry out the invention, the blood flow cavity 32 must be elongated between the openings 56 and 58 leading into and out of the blood flow cavity 32, and also be constructed in a configuration that will not lead to excessive clotting, air pockets in the blood in the viewing area 32 or hemolysis.

Referring now to FIGS. 3 and 7, the lens body 26 has a circular viewing lens 38, as mentioned earlier with respect to FIG. 5. The overall shape of the lens body 26 and in particular the dimensions of its outer perimeter provide a mating fit to the chamber body 26 in order to ensure that the lens body 26 is secured to the chamber body 24 in the proper orientation when the lens body 26 is sonically welded to the chamber body 24. More specifically, the lens body 26 is preferably welded into place on a receiving ledge 60, see FIG. 3, which extends around the edge of the peripheral wall 50 opposite the internal flat wall 46 on the chamber body 24. The openings 56, 58 in the peripheral wall are substantially circular except for a horizontal cord which is parallel to and offset from the receiving ledge 60, and when the lens body 26 is welded in place, also parallel to and offset from the flat internal wall 48 on the lens body 26 forming part of the internal flow cavity 32. The nominal diameter of the openings 56, 58 is set to be equal to the preferred distance between the flat wall 46 on the chamber body 24 and the flat wall 48 on the lens body 26, which is 0.083", also happens to be substantially the same distance across the inside diameter of the ⅛" tubing, see reference number 63 in FIG. 8. In order to accommodate the required spacing between the internal walls 46 and 48, the structure of the chamber body comprising the receiving ledge 60 and in particular the portion spanning over the openings 56, 58 dips into the channels 30, 36 to form the horizontal chords in openings 56, 58 mentioned above.

At low flow rates (e.g. 10 to 500 ml/min), conventional blood chambers show a tendency to clot more often than desired. On the other hand blood flow cavity 32 configured in accordance with the preferred embodiment of the invention as described has been found to provide robust non-linear flow of homogeneous blood through the blood cavity at low flow rates (e.g. 10 to 500 ml/min.) without giving rise to clotting, air bubbles or hemolysis issues. The preferred radius of the arcuate portions of the peripheral wall 52 is 3.6 inches. The preferred distance between the openings 56, 58 is about 0.621 inches, and the maximum perpendicular distance across the blood flow cavity 32 between the arcuate portions of the peripheral wall is about 0.46 inches.

The radius of the circular viewing area in the lens body 38, is preferably about 0.24 inches which is substantially the same as on a conventional blood chamber. At the same time, the overall volume of the blood flow cavity 32 is much smaller than in a conventional blood flow chamber.

Referring in particular to FIGS. 2, 3 and 6 the lens body 26 includes upstanding pedestals 62 axially disposed along the lens body 26 and generally located above the channels 30, 36 and openings 56, 58 when the lens body 26 is welded into place on the chamber body 24. The pedestals 62 extend outward from a sensor receiving wall 64 on the lens body 26. The sensor receiving wall 64 is substantially parallel to the circular lens 38 for the viewing area, and provides an opening for the viewing lens 38 to be exposed to the sensor 42A. As shown in FIGS. 2 and 5, when the lens body 26 is welded into place in the chamber body 24, the receiving ledge 64 is detented relative to the overall blood chamber 12. The upstanding pedestals 62 serve to guide the sensor 42A on the sensor clip assembly 10 into proper alignment when the sensor 42A is clipped against the receiving ledge 64. This configuration results in the face of the sensor 42A being exposed in proper parallel and rotational orientation with respect to the circular viewing lens 38.

Figure 8:
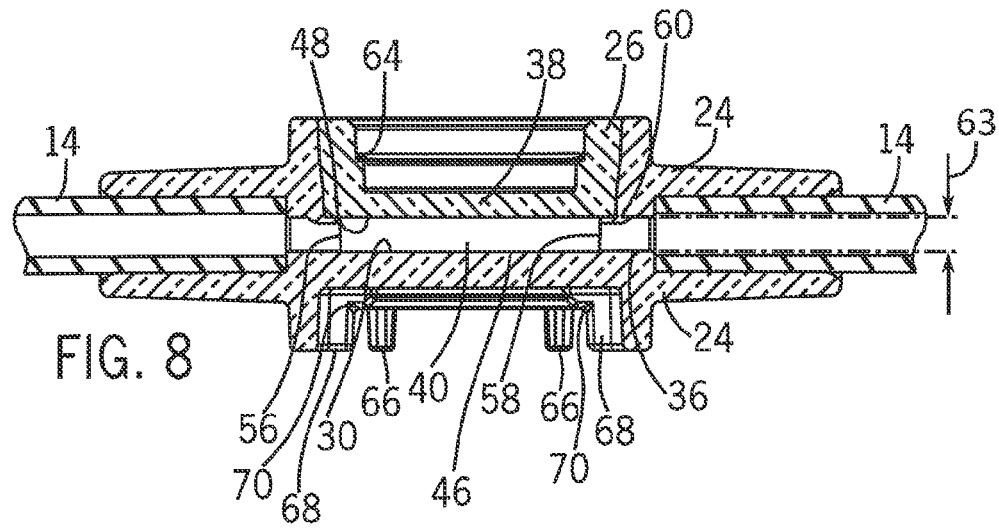
FIG. 8 is a longitudinal sectional view of the blood chamber only as taken along line 5-5 in FIG. 1.

Referring now in particular to FIGS. 4, 5, and 8, the chamber body 24 includes detented receiving ledges 70 on either side of the circular viewing area 40. The chamber body 24 also includes upstanding finger 66 and guide walls 68 which serve to guide the photodetector 42B on arm 16B of the sensor clip assembly 10 into proper alignment when the clip sensor assembly is clipped onto the blood chamber 12. It should be noted that FIGS. 1 and 5 show the sensor clip assembly 10 clipped onto the blood chamber 12 with the photodetectors 42B on the left hand side and the photoemitters 42A on the right hand side. The dimensional characteristics of the right side 16A and the left side 16B of the sensor assembly 10 are normally congruent, however the blood flow chamber 12 is designed to be used with the photodetectors 42B on either the right or left hand side with the photoemitters 42A being on the opposite side.

Figure 9:
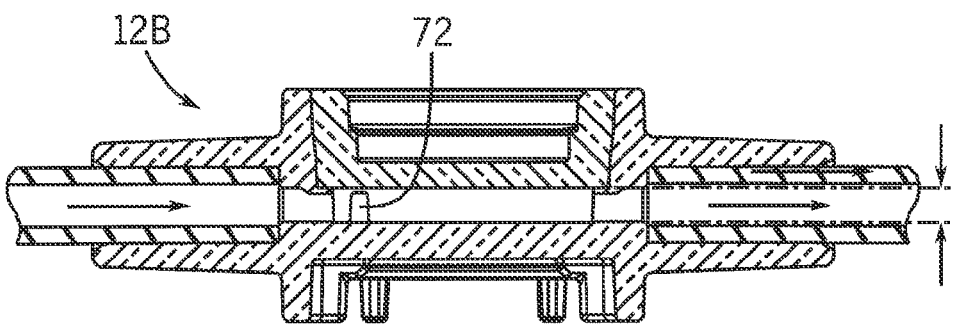
FIG. 9 is a sectional view similar to that shown in FIG. 8, showing another embodiment of the invention utilizing turbulence posts.

FIG. 9 shows blood chamber 12B constructed in accordance with another embodiment of the invention. Referring now to FIG. 9, it may be desirable to include a pair of turbulence post 72 at the upstream end of the blood flow cavity 32. While the flow through the blood chamber 12 is shown in FIGS. 1-8, has been found to be sufficiently mixed and robust, it may be desirable to include turbulence posts 72 to enhance mixing within the blood flow cavity 32 prior to viewing.

Figure 10:
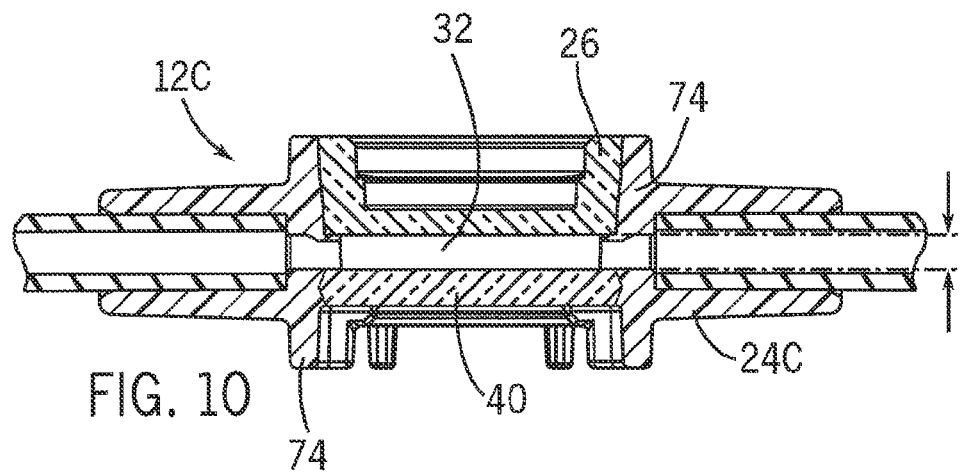
FIG. 10 is a sectional view similar to FIGS. 8 and 9 showing yet another embodiment of the invention in which the chamber body is made of a blue-tinted opaque material except for the lens in the chamber body which is made of a transparent material.

FIG. 10 illustrates a blood chamber 12C constructed in accordance with another embodiment of the invention in which much of the chamber body 24C is made of blue-tinted material (portion 74), except for a clear circular lens portion 40. The purpose of constructing part of the chamber body 24C with a blue-tinted material is to reduce the effects of light ducting of red light at 660 nm. For this purpose, it is desirable that the blue-tinted chamber body 24C block light transmission at the 660 nm wavelength, as disclosed in co-pending U.S. patent application Ser. No. 12/876,572, entitled "Blood Chamber for an Optical Blood Monitoring System", filed on even date herewith by the assignee of the present application and incorporated herein by reference. Preferably, the chamber body as in the prior embodiments is made from a medical grade polycarbonate. However, in the blood chamber 12C shown in FIG. 10 the circular lens portion 40 on the chamber body 24C is first molded from a clear material, and the remainder 74 of the chamber body 24C is molded from an opaque material via an overmolding process.

Note that the blood chamber 12C in FIG. 10 does not include a moat surrounding the blood flow cavity 32 as in the prior art blood chambers. As mentioned, in the prior art, the moat is useful to prevent errors arising because of light ducting or ambient light. While errors arising from light ducting should not normally be an issue if the chamber body 24 is made of clear polycarbonate material using the design shown in FIGS. 1-9, a blue-tinted chamber body 24C can be used if light ducting at 660 nm does become a problem in a given application.

It is to be expected that various equivalents, alternatives and modifications are possible within the scope of the appended claims.

What is claimed is:

1. A blood chamber for optically monitoring blood flowing through an extracorporeal tube, the blood chamber defining a flow path through an internal blood flow cavity which provides a viewing area for optical monitoring of the blood, the blood chamber comprising:
    a chamber body having a flat internal wall with at least a first perimeter edge and a second perimeter edge, and a peripheral wall extending around the flat internal wall, the peripheral wall including first and second portions commensurate with the first and second perimeter edges of the flat internal wall,
        a first port and channel in fluid communication with a first opening in the peripheral wall of the blood chamber,
        a second port and channel in fluid communication with a second opening in the peripheral wall of the blood chamber, the second port and channel being in axial alignment with the first port and channel along an axis across the blood chamber, wherein the distance across a blood chamber between the first and second openings in the peripheral wall is greater than the maximum distance perpendicular to the axis across the blood chamber between the first and second portions of the peripheral wall; and
    a lens body having a flat internal wall that is attached to the chamber body to form the internal blood flow cavity, wherein the lens body is attached to the chamber body with the flat internal wall on the lens being substantially parallel to the flat internal wall on the chamber body and also being separated from the flat internal wall in the chamber body by a predetermined fixed distance,
    wherein the lens body has an outside surface with a detented receiving ledge for receiving the face of a first extended foot on the housing of one side of an optical sensor clip assembly and the chamber body has an outside surface with a detented receiving ledge for receiving the face of a second extended foot on the housing of another side of the optical sensor clip assembly, and wherein the shape of the first and second feet are substantially the same.

2. A blood chamber as recited in claim 1 wherein:
    the perimeter edges of the flat internal wall of the chamber body are arcuate; and
    the first and second portions of the peripheral wall of the chamber body are arcuate.

3. A blood chamber as recited in claim 1 wherein the lens body comprises a flat, circular viewing lens that is spaced apart from the detented receiving ledge on the lens body.

4. A blood chamber as recited in claim 3 wherein the lens body includes first and second upstanding pedestals for guiding the clip assembly into proper alignment, each pedestal extending outwardly from the detented receiving ledge and located axially between the viewing lens and a respective port.

5. A blood chamber as recited in claim 1 wherein the chamber body includes multiple upstanding fingers spaced around the periphery of the detented receiving ledge for guiding the clip assembly into proper alignment.

6. A blood chamber as recited in claim 1 in which the first and second ports are sized to be connected to 1/8" extracorporeal tubing capable of sustaining blood flow at rates of 10 to 500 ml/min.

7. A blood chamber as recited in claim 1 in which the first port is sized to be connected to 1/8" extracorporeal tubing capable of sustaining blood flow at rates of 10 to 500 ml/min and the second port is an attached or molded industry standard luer lock connector.

8. A blood chamber as recited in claim 1 in which the first and second ports are sized to be capable of sustaining blood flow at rates of 10 to 500 ml/min and attached to or molded with industry standard luer lock connectors.

9. A blood chamber as recited in claim 1 wherein the first and second opening in the peripheral wall are substantially circular except for a horizontal chord which is parallel to and offset from the flat wall on the lens body forming the internal flow cavity.

10. A blood chamber as recited in claim 1 further comprising a pair of turbulence post extending upward from the internal flat surface of the chamber body into the internal blood flow cavity in the vicinity of the opening in the peripheral wall from the first port and channel.

11. A blood chamber as recited in claim 1 wherein the chamber body includes a clear polycarbonate viewing lens having a circular shape and the remainder of the chamber body is made of an opaque polycarbonate material.

12. A blood chamber as recited in claim 11 wherein the entire lens body is made of a clear polycarbonate material.

* * * * *